United States Patent [19]

Brodack et al.

[11] Patent Number: 5,662,882
[45] Date of Patent: Sep. 2, 1997

[54] RADIOPHARMACEUTICAL FORMULATIONS HAVING NON-STANNOUS REDUCTANTS

[75] Inventors: James W. Brodack, Florissant; Mark A. DeRosch, St. Charles; Edward A. Deutsch; Mary Marmion Dyszlewski, both of Maryland Heights, all of Mo.

[73] Assignee: Mallinckrodt Medical, Inc., St. Louis, Mo.

[21] Appl. No.: 410,642

[22] Filed: Mar. 23, 1995

Related U.S. Application Data

[63] Continuation of Ser. No. 40,739, Mar. 31, 1993, abandoned.

[51] Int. Cl.$^6$ ............................................. A61K 51/00
[52] U.S. Cl. ..................... 424/1.11; 424/1.65; 424/1.77
[58] Field of Search .......................... 424/1.11, 1.65, 424/1.77

[56] References Cited

U.S. PATENT DOCUMENTS

| | | | |
|---|---|---|---|
| 3,749,556 | 7/1973 | Barak | 424/1.1 |
| 4,208,398 | 6/1980 | Kubiatowicz et al. | 424/1.1 |
| 4,272,503 | 6/1981 | Camin et al. | 424/1 |
| 4,314,986 | 2/1982 | Ruddock | 424/1.1 |
| 4,642,229 | 2/1987 | Cumming et al. | 424/1.1 |
| 4,795,626 | 1/1989 | Deutsch et al. | 424/1.1 |
| 4,810,486 | 3/1989 | Kelly et al. | 429/1.1 |
| 4,873,074 | 10/1989 | Chia et al. | 424/1.1 |
| 4,925,650 | 5/1990 | Nosco et al. | 424/1.1 |
| 4,957,728 | 9/1990 | Deutsch et al. | 424/1.1 |
| 5,069,900 | 12/1991 | Linder | 424/1.1 |
| 5,112,594 | 5/1992 | Woulfe et al. | 424/1.1 |
| 5,202,109 | 4/1993 | Fritzberg et al. | 424/1.1 |
| 5,300,280 | 4/1994 | DeRosch et al. | 424/1.53 |
| 5,317,091 | 5/1994 | Subramanian | 424/1.53 |

*Primary Examiner*—Gary E. Hollinden
*Assistant Examiner*—Lara E. Chapman
*Attorney, Agent, or Firm*—Wendell Ray Guffey; Thomas P. McBride

[57] ABSTRACT

The present invention relates to novel radiopharmaceutical imaging agents having non-stannous reductants. The present invention further relates to kits for forming radiopharmaceutical imaging agents, such kits including non-stannous reducing agents.

7 Claims, No Drawings

RADIOPHARMACEUTICAL FORMULATIONS HAVING NON-STANNOUS REDUCTANTS

This is a continuation of Ser. No. 08/040,739 filed on Mar. 31, 1993, now abandoned.

BACKGROUND

The present invention relates to novel radiopharmaceutical imaging agents having non-stannous reductants. The present invention further relates to kits for forming radiopharmaceutical imaging agents, such kits including non-stannous reducing agents.

Several non-invasive methods of imaging skeletal structures, and body organs and tissues have been developed over the past decades. These methods are based on the tendency of the particular skeleton, organ or tissue to concentrate certain chemicals which may be detectable, such as through the use of scintiphotography or radiation detection. The use of radiopharmaceutical imaging agents in imaging skeletal structures, organs and tissues, is well known in the fields of biological and medical research as well as diagnostic evaluation procedures. Metal-based radiopharmaceuticals, such as those based on technetium have been found to provide particularly useful images of skeletal structures, and body organs and tissues from which diagnostic information may be obtained. More particularly, radiopharmaceuticals based on technetium 99m have been used successfully as diagnostic imaging agents.

In addition, metal-based radiopharmaceuticals, such as those based on rhenium have been found to be useful as therapeutic agents in the treatment of various diseases. More particularly, radiopharmaceuticals based on rhenium 186 or rhenium 188 have been used sucessfully as therapeutic agents.

The radiopharmaceutical agents generally include a metal radionuclide, various ligands for binding the radionuclide to the desired skeletal structure, organ or tissue, reducing agents, stabilizing agents, carriers and delivery vehicles suitable for injection into, or aspiration by a patient, etc.

Because of the relatively short half-lives of the metal radionuclide used in the radiopharmaceutical agent, it is desirable to provide the non-radioactive components of the agent as a kit to which a radionuclide containing solution may be added to form the agent. In particular, a radionuclide generator may be employed in a known manner to obtain a radionuclide which may then be combined and reacted with the contents of a kit which contains appropriate radiopharmaceutical forming components. For example, when forming a technetium imaging agent, a pertechnetate solution may be obtained from a technetium generator. The pertechnetate solution may then be combined and reacted with the components of a kit containing the other materials and agents necessary for forming the radiopharmaceutical agent.

A reducing agent is a necessary component of many radiopharmaceutical kits, the reducing agent acting to reduce the radionuclide containing solution, such as a pertechnetate solution, to obtain the final radiopharmaceutical agent. A reducing agent must be included in kits for the formation of technetium radiopharmaceuticals. Stannous ion is the most widely used reducing agent in kits for forming metal-based radiopharmaceuticals. This includes known kits for forming technetium 99m diagnostic agents for imaging the heart, kidney, lungs, and hepatobiliary system, as well as kits for imaging and therapeutic treatment of the brain and skeleton. However, the use of stannous ion as a reducing agent has several disadvantages generally arising from the inherent problems related to the complicated solid and solution chemistry of stannous compounds. In particular, the stannous ion is often a "non-innocent" reducing agent which interferes with or is incorporated into the final radiopharmaceutical.

Therefore it is desirable to provide radiopharmaceutical forming kits which contain non-stannous reducing agents.

OBJECT OF THE INVENTION

It is one object of the present invention to provide radiopharmaceutical formulations having non-stannous reductants.

It is another object of the present invention to provide kits for forming radiopharmaceutical agents, such kits including non-stannous reducing agents.

SUMMARY OF THE INVENTION

The above objects and others are achieved by providing a kit for forming radiopharmaceutical agents, wherein the kits include non-stannous reducing agents.

DETAILED DESCRIPTION OF THE INVENTION

The use of stannous ion as a reductant for preparation of radiopharmaceutical agents is well known. Therefore, stannous ion is commonly included as a component of kits for forming radiopharmaceutical agents, such as agents for imaging the heart, kidneys, lungs and hepatobiliary system and agents for imaging and therapeutic treatment of the brain and skeleton.

However, the use of stannous ion as a reducing agent in the formation of radiopharmaceutical agents has several disadvantages. In particular, stannous compounds have inherent disadvantages associated with their complicated solid and solution chemistry. For example, stannous ion often acts as a "non-innocent" reductant and may interfere with the formation of the final radiopharmaceutical agent, or become incorporated into the final radiopharmaceutical agent.

It has been discovered that there are a number of pharmaceutically acceptable non-stannous reducing agents which do not possess the same disadvantages of using stannous ion as a reducing agent in the formation of radiopharmaceutical agents.

In particular, metallic compounds, such as Cu(I), Cu(II), Co(II), Fe(II), Sn(0), Zr(0), Cr(II) and Zn(0), will act to effectively reduce a radionuclide containing solutions, such as pertechnetate solutions, to obtain the desired final radiopharmaceutical agent.

Further, several non-metallic compounds, such as acids in general, dithionite, formamidine, formamadine sulfinic acid, phosphite, hypophosphite, dithiothreitol, hydrochloric acid, and borohydric acid, may also be effectively used to reduce radionuclide containing solutions.

Moreover, it has been discovered that several agents, such as phosphines, sulfhydryl compounds, phosphites, thiols, thioethers, borates, borocyano groups, ascorbates, and gentisates, efficiently reduce the radionuclide containing solution and complex with the radionuclide at the same time. This is very advantageous in reducing the number of components that must be included in kits for forming radiopharmaceuticals, and in simplifying the chemistry needed to produce the final radiopharmaceutical agent.

According to one embodiment of the present invention, a kit for forming a technetium myocardial imaging agent includes tris(3-methoxypropyl)phosphine (TMPP), as both a reducing agent and as a complexing agent. Further components, such as cuprous ascorbate, may also be included in the kit to increase radiopharmaceutical yield. Notably, it has been found that the addition of stannous ion to the kit actually reduces the product yield by forming reduced hydrolyzed technetium as a by-product.

In a further embodiment of the present invention, a kit for forming radiopharmaceutical imaging agents includes tertiary phosphines ($PR_3$) wherein the phosphine also acts as a ligand for the technetium complex. In particular, it has been discovered that $^{99m}Tc(VII)O_4^-$ may be reduced using a monodentate phosphine, such as, tertiary phosphines in the presence of a Schiff base ligand (L4). The kit may be a lyophilized kit containing the tertiary phosphine, the Schiff base ligand, and a buffer, but does not require ancillary reductants such as stannous ion, hypophosphite, or ascorbate to carry out the reduction reaction, if the technetium-99m generator eluant is degassed prior to its use. It is believed that the reduction reaction proceeds through a $^{99m}Tc(V)$ intermediate, such as $^{99m}Tc(V)(O)(L4)^+$, to ultimately form $^{9m}Tc(III)(L4)(PR_3)_2^+$, as a myocardial imaging agent.

In addition, in accordance with the present invention, it has been discovered that hypophosphite ion $(H_2PO_2)^-$ may be used as an antioxidant and reductant in the formation of Tc-99m radiopharmaceuticals. The reduction potential for hypophosphite ion is comparable to ascorbic acid. Further, the oxidation product of hypophosphite is phosphite, $PO_3^{3-}$, which is totally innocuous in Tc-99m radiopharmaceutical preparations. Hypophosphite and phosphite are totally colorless, easy to analyze, lyophilizable, and injectable.

In another embodiment according to the present invention, it has been discovered that hydrogen phosphite ($HPO_3^{2-}$) may be used as an antioxidant and reductant in the formation of Tc-99m radiopharmaceuticals. The reduction potential for hydrogen phosphite is comparable to ascorbic acid. Further, the oxidation product of hydrogen phosphite is phosphate, $PO_4^{3-}$, which is totally innocuous in Tc-99m radiopharmaceutical preparations. Phosphite and phosphate are colorless, easy to analyze, lyophilizable, and injectable.

The foregoing has been a description of certain preferred embodiments of the present invention, but is not intended to limit the invention in any way. Rather, many modifications, variations and changes in details may be made within the scope of the present invention.

What is claimed is:

1. In a method for forming a radiopharmaceutical imaging agent, the improvement comprising combining a non-reduced radionuclide solution with a multidentate ligand and a chemical agent, the chemical agent reducing the radionuclide and complexing with the radionuclide in a manner incorporating the chemical agent into the radiopharmaceutical imaging agent.

2. The method of claim 1 wherein the multidentate ligand is a Schiff base ligand.

3. The method of claim 2 wherein the chemical agent is selected from the group consisting of phosphines, sulfhydryl compounds, phosphites, thiols, thioethers, borates, borocyano groups, ascorbates and gentisates.

4. The method of claim 3 wherein the chemical agent is a phosphine.

5. The method of claim 4 wherein the phosphine is a tertiary phosphine.

6. The method of claim 5 wherein the tertiary phosphine is tris(3-methoxropyl)phosphine.

7. The method of claim 6 wherein the non-reduced radionuclide pertechnetate-99m.

* * * * *